US 6,676,693 B1

(12) United States Patent
Belding et al.

(10) Patent No.: US 6,676,693 B1
(45) Date of Patent: Jan. 13, 2004

(54) APPARATUS AND METHOD FOR DELIVERING A SELF-EXPANDING STENT

(75) Inventors: Brent Belding, Los Gatos, CA (US); Steve Bigus, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 102 days.

(21) Appl. No.: 09/892,670

(22) Filed: Jun. 27, 2001

(51) Int. Cl.[7] .................................................. A61F 2/06
(52) U.S. Cl. ..................................... 623/1.11; 606/108
(58) Field of Search .............................. 623/1.11, 1.2, 623/1.23; 606/108, 191, 192, 194, 195; 604/523, 524, 525, 526, 527

(56) References Cited

U.S. PATENT DOCUMENTS

| 5,458,615 A | * | 10/1995 | Klemm et al. ......... 604/103.04 |
| 5,534,007 A | | 7/1996 | St. Germain et al. |
| 5,735,859 A | * | 4/1998 | Fischell et al. ............. 606/108 |
| 5,772,669 A | | 6/1998 | Vrba |
| 5,891,154 A | * | 4/1999 | Loeffler ....................... 606/194 |
| 5,910,145 A | * | 6/1999 | Fischell et al. ............. 606/108 |
| 5,928,258 A | | 7/1999 | Khan et al. |
| 6,143,016 A | | 11/2000 | Bleam et al. |

* cited by examiner

Primary Examiner—Corrine McDermott
Assistant Examiner—William H Matthews
(74) Attorney, Agent, or Firm—Fulwider Patton Lee & Utecht, LLP

(57) ABSTRACT

An assembly for delivering a self-expanding stent to an intraluminal location comprising a sheath having a generally non-compliant first portion and a compliant second portion, with the stent positioned within the generally non-compliant first portion for stent delivery. Upon stent deployment, the stent passes from the generally non-compliant first portion into the compliant second portion, and then out of the sheath. The compliant second portion permits the stent to at least partially expand before it passes out of the sheath, so that the force with which the stent expands once outside the sheath is tempered.

6 Claims, 3 Drawing Sheets

APPARATUS AND METHOD FOR DELIVERING A SELF-EXPANDING STENT

BACKGROUND OF THE INVENTION

The invention relates generally to a system and method for delivering a stent. More particularly, the invention relates to a stent delivery system (SDS) and method for delivering a self-expanding stent into a body lumen.

In typical percutaneous transluminal coronary angioplasty (PTCA) procedures, a guiding catheter having a preformed distal tip is percutaneously introduced into the cardiovascular system of a patient through the brachial or femoral arteries and is advanced therein until the distal tip thereof is in the ostium of the desired coronary artery. A guide wire and a dilatation catheter having an inflatable balloon on the distal end thereof are introduced through the guiding catheter with the guide wire slidably disposed within an inner lumen of the dilatation catheter. The guide wire is first advanced out of the distal end of the guiding catheter and is then maneuvered into the patient's coronary vasculature containing the lesion to be dilated, and is then advanced beyond the lesion. Thereafter, the dilatation catheter is advanced over the guide wire until the dilatation balloon is located across the lesion. Once in position across the lesion, the balloon of the dilatation catheter is filled with radiopaque liquid at relatively high pressures (e.g greater than about 4 atmospheres) and is inflated to a predetermined size (which may be the same as the inner diameter of the artery at that location) to radially compress the atherosclerotic plaque of the lesion against the inside of the artery to thereby dilate the lumen of the artery. The balloon is then deflated so that the dilatation catheter can be removed and blood flow resumed through the dilated artery.

A common problem that sometimes occurs after an angioplasty procedure is the appearance of restenosis at or near the site of the original stenosis in the blood vessel which requires a secondary angioplasty procedure or a bypass surgery. Another occurrence which reduces the success of an angioplasty procedure is that frequently the stenotic plaque or intima of the blood vessel or both are dissected during the angioplasty procedure by the inflation of the balloon. Upon deflation of the balloon, a section of the dissected lining (commonly called a "flap") will collapse into the bloodstream, thereby closing or significantly reducing the blood flow through the vessel. In these instances, emergency bypass surgery is usually required to avoid a myocardial infarct distal to the blockage. Side branches, tortuous vessels, and the more distal arteries have also presented serious difficulties in the PTCA procedure because of the balloon diameter.

Conceivably, the dilatation catheter could be replaced with a perfusion type dilatation catheter such as described in U.S. Pat. No. 4,790,315 in order to hold the blood vessel open for extended periods. However, perfusion type dilatation catheters have relatively large profiles which can make advancement thereof through the blockage difficult, and therefore immediate bypass surgery may be the only means of avoiding an infarct distal to the blockage or possibly even death. Additionally, the inflated balloon of these perfusion catheters can block off a branch artery, thus creating ischemic conditions in the side branch distal to the blockage.

In response, one particular endoprosthetic device, known as a stent, has been developed to prevent restenosis and repair damaged vessel walls. Stents are generally tubular shaped intravascular devices having an expandable or self-expanding structure that is placed within a damaged artery to hold it open. They are particularly suitable for supporting and holding back a dissected arterial lining which could otherwise occlude the fluid passageway there through. The use of stents in non-invasive interventional cardiology has proven to have many advantages, including a net gain in Minimal Lumen Diameter (MLD) of the vessel and reduced restenosis rates.

Stents typically are constructed in one of two general configurations: expandable, and self-expanding. Expandable stents require a mechanical force, such as exerted by a balloon disposed within the stent interior, to increase in diameter. Self-expanding stents are generally constructed of shape memory materials that are biased so that the stent diameter will increase from a reduced diameter maintained by constraining forces to an expanded diameter once the constraining forces are removed, without the action of any external mechanical forces.

Self-expanding stents may be formed in a variety of configurations, and such stents made of coiled wire or springs, braided wire or mesh, and fence-like structures configured in a zig-zag pattern are known in the art. Examples of such of these stents can be found in U.S. Pat. Nos. 4,655,771 (Wallsten); 5,405,380 (Gianotti et al.); 5,709,703 (Lukic et al.); and 5,735,871 (Sgro).

Delivery systems for self-expanding stents are generally comprised of a stent circumferentially surrounding the distal end of a delivery catheter. Due to the narrow passageways within the vascular system and particularly the stenotic regions, stents are generally confined in a reduced radius for delivery to the deployment site. Therefore, it is highly desirable to keep the profile of the catheter as small as possible to minimize the radius of the stent mounted thereon. For delivery purposes, these stents are typically held in a minimal diameter state by some structure such as a sheath. Upon displacement of the sheath, the stent is exposed to self-expand and contact the vessel wall. Once the stent is deployed, the catheter is removed, leaving the stent implanted at the desired location to keep the vessel walls from closing and allowing time to heal. Examples of devices of this type can be found in U.S. Pat. Nos. 5,690,644 (Yurek et al.) and 5,735,859 (Fischell et al.). Another device, as exemplified in U.S. Pat. No. 5,372,600 (Beyar et al.), secures the stent to a catheter without the use of a sheath.

The choice of using a self-expanding stent delivery system instead of a balloon catheter is not without tradeoffs. Stent delivery systems for self-expanding stents using a delivery catheter can have larger profiles, be less flexible, and generally feel more cumbersome than their balloon counterparts. Achieving smooth, even expansion of the self-expanding stent can be difficult, in that some self-expanding stents have a tendency to spring outward to their maximum radius when released. This springing action can cause the stent to jump distally in the artery, which, depending on the amount of distal movement of the stent, can displace the stent from its desired deployment location. Additionally, the unconstrained expansion of a self-expanding stent can result in the self-expanding stent contacting the arterial wall with some amount of force.

What has been needed and heretofore unavailable is an improved stent delivery system capable of securing and delivering a self-expanding stent on a catheter or other delivery device and smoothly releasing the self-expanding stent so that it smoothly and gradually expands to its full expanded size. The present invention satisfies these needs as well as others.

SUMMARY OF THE INVENTION

The present invention is directed to a device and method for delivering a self-expanding stent using a variable-strength sheath to restrain the self-expanding stent, which is particularly suitable for use in coronary arteries to hold vessels open after a balloon angioplasty procedure.

The variable-strength sheath stent delivery system in accordance with the present invention includes a sheath having a first portion and a second portion. The first portion is able to flex in order to traverse tortuous lumens, but has relatively little or no compliance (that would otherwise permit a self-expanding stent within the first portion to expand radially outwardly.) A stent positioned with the first portion can not appreciably expand. The second portion of the sheath has a higher compliance, so that it can permit at least some level of expansion of a self-expanding stent positioned within the second portion. By controlling initial expansion of the stent, the sheath provides a transition between the constrained delivery diameter of the stent and the unconstrained deployed diameter of the stent. Distal jumping of the stent during deployment is prevented. The sheath also tempers the final expansion of the stent as it completely exits the sheath, thereby preventing the stent from expanding with too much force into the vessel walls.

In one embodiment of the invention, the self-expanding stent is forced into a constrained position having a low profile or reduced cross section and positioned within the first (i.e., generally non-compliant) portion of the variable-strength sheath. The sheath and stent are then introduced into a body lumen and advanced to the treatment site. Once the stent is in the desired position, the stent may be slid out of the first non-compliant portion, into the compliant portion, and out of the sheath. The sliding out of the stent may be accompanied by a simultaneous, equal, and/or and opposite withdrawal of the sheath from the treatment site, so that the stent remains distally motionless with respect to the treatment site. As the stent enters the compliant portion, it can begin to expand. When the stent exits the sheath, the stent can fully deploy into contact with the arterial wall and provide structural support thereto.

In an embodiment where the stent is held fixed, the sheath slides proximally relative to the desired treatment location, with the stent remaining still with respect to the treatment/deployment location. As the sheath is retracted, the stent expands progressively, so that the distal portion of the stent expands to the diameter of the more compliant sheath section while the remainder of the stent is constrained at the original diameter by the non-compliant sheath section.

In one embodiment of the invention, the compliance of the second portion varies across the length of the second portion. The compliance or the ability of the material to resist applied pressure without changing dimensions, may be less at a proximal end of the second portion, and greater at a distal end of the second portion. The variation in compliance may be achieved by varying the thickness of the second portion, such as by having reduced thickness at the distal end of the second portion or by changing material or material properties such as orientation or crystalinity. The first and second portions may be formed from the same material, with the second portion having less thickness than the first portion.

In one embodiment, the stent is slid out of the sheath by the use of a deployment device, such as a rod, that pushes the stent out of the sheath. The deployment device may push against the stent's proximal end to push the stent out of the sheath. The deployment device may also serve to prevent a stent from moving proximally as the sheath is withdrawn in the proximal direction from over the stent.

In another embodiment, the stent is positioned on an elongated device, such as a delivery catheter, and the sheath is placed over the stent and elongated device so that the stent is positioned within the generally non-compliant first portion of the sheath. When the sheath is withdrawn from over the stent, as may be achieve by sliding the sheath proximally along the elongated device, the stent is released and can expand.

The present invention also relates to a method of implanting a self-expanding stent using a sheath according to the invention. A stent delivery system is provided with sheath encircling a self-expanding stent. The stent is secured in a compressed, reduced profile configuration in the first portion of the sheath until deployment. The stent delivery system is inserted into a vessel and advanced to a treatment site. The sheath is axially displaced in the vessel as the stent is slid out of the sheath, so that the stent remains axially stationary with respect to the vessel. As the stent slides into the compliant second portion, the stent begins to gradually expand. As the stent exits the sheath entirely, it deploys against the vessel wall by self-expansion. The sheath is then withdrawn from the vessel leaving the deployed stent in place.

Other features and advantages of the present invention will become more apparent from the following detailed description of the invention, when taken in conjunction with the accompanying exemplary drawings.

BRIEF DESCRIPTION OF THE DRAWINGS

FIG. 7b is a side is a side view, in partial cross-section, of the sheath of FIG. 7a.

DETAILED DESCRIPTION OF THE PREFERRED EMBODIMENTS

The present invention relates to a stent delivery system in which a self-expanding stent is delivered into a human patient's body lumen, such as a coronary artery, carotid artery, renal artery, or peripheral artery or vein. The invention provides a stent delivery system and method of use in which a stent is implanted in a patient.

Figure 1:
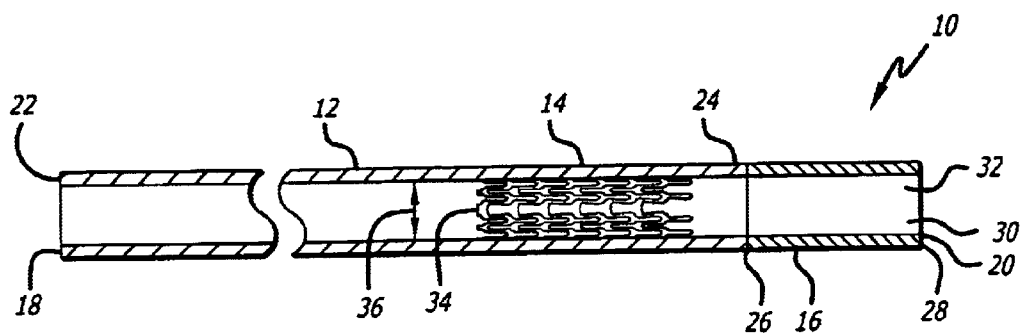
FIG. 1 is a side view, in partial cross-section, of a stent delivery system according to the present invention.

For purposes of illustration, FIG. 1 depicts a stent delivery system 10 according to an embodiment of the invention. Generally, stent delivery system 10 includes a generally tubular sheath 12 with a generally non-compliant first portion 14 and a generally compliant second portion 16. The tubular sheath 12 terminates in a proximal end 18 and a distal end 20.

The non-compliant first portion 14 itself has a first portion proximal end 22 (which in the embodiment depicted corresponds to the sheath proximal end 18) and a first portion distal end 24. Adjacent the first portion distal end 24 is the proximal end 26 of the compliant second portion 28. The non-compliant first portion 14 and compliant second portion 16 are connected together to define a lumen 30 that runs through at least a part of the sheath 12. The lumen 30 terminates in a distal opening 32 at the sheath distal and 20 (which is also the compliant second portion distal end 28).

The non-compliant first portion 14 may be longitudinally flexible so that it can bend to traverse tortuous arteries and other non-straight blood vessels. The first portion may also be resistant to compression and/or tension along its length, so that axial movement of the proximal end 22 of the first portion 14 will cause similar axial movement of the distal end 24 of the first portion 14.

The compliant second portion 16 maybe longitudinally flexible, and may also be relatively compressible and stretchable in the longitudinal direction. Such flexibility, stretchability, and compressibility may improve the performance of the sheath by permitting the compliant second portion more easily adapt to a tortuous anatomy, and may also serve to reduce trauma from any contact between the compliant second portion 14 and a vessel wall, such as contact that may occur as the sheath 12 is introduced into a patient's arterial system.

Positioned within the first portion 14 of the sheath 12 is a self-expanding stent 34. The self-expanding stent 34 has an unexpanded or delivery diameter 36 defined by the diameter of the sheath inner lumen.

Figure 2:
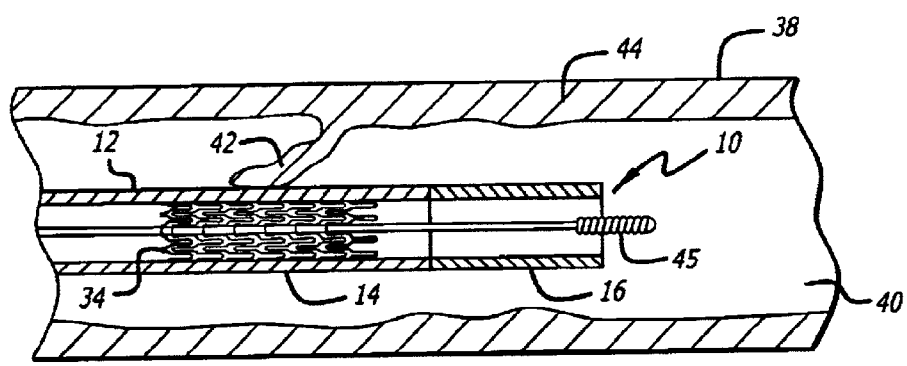
FIG. 2 is a side view, in cross-section, of a stent delivery system according to the present invention used to deploy a stent in a vessel.
Figure 3:
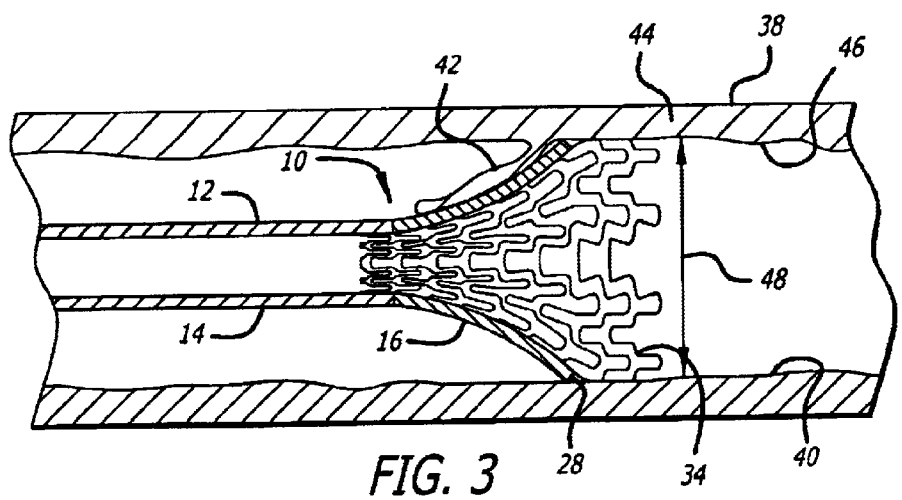
FIG. 3 is a side view, in cross-section, of the stent delivery system of FIG. 2 used to deploy a stent in a vessel.
Figure 4:
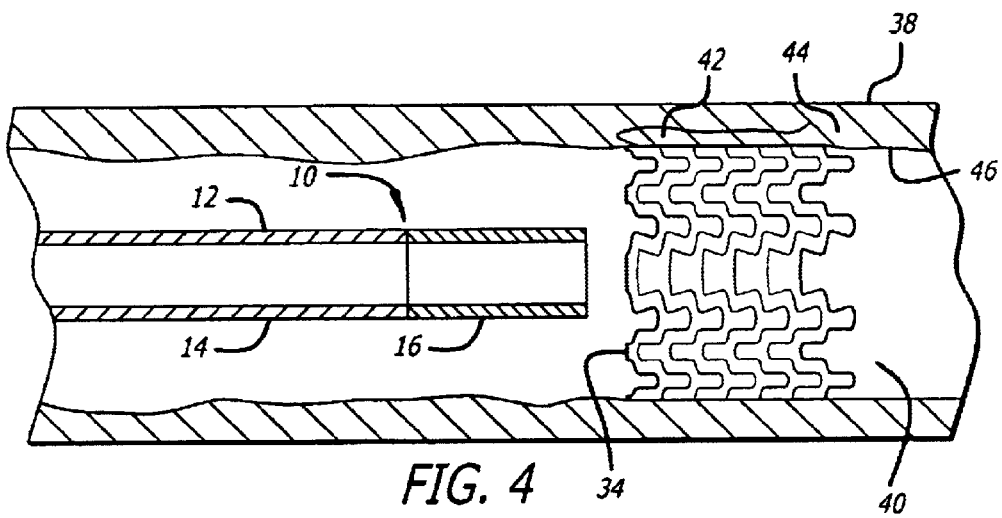
FIG. 4 is a side view, in cross-section, of a stent delivery system of FIG. 2 used to deploy a stent in a vessel.

FIGS. 2 through 4 illustrate, by way of example, a method of delivering and implanting a self-expanding stent 34 using the current invention. FIGS. 2–4 illustrate a situation in which the stent delivery system 10 having a tubular sheath 12 is used to deploy a self-expanding stent 34 to treat an artery 38 where the arterial lumen 40 is blocked, in whole or in part, by a dissection 42 that has come loose from the arterial wall 44. The procedures and devices described herein may be adapted by one of ordinary skill in the art to any procedure where a self-expanding endoprosthesis is to be placed into a body lumen.

As shown in FIG. 2, a stent delivery assembly 10 is provided with tubular sheath 12 with a self-expanding stent 34 positioned in the generally non-compliant first portion 14. The stent delivery assembly 10 is inserted into the lumen 40 of an artery 38 along a guidewire 45, with the guidewire 45 having been previously positioned in proximity to the dissection 42 requiring support. The sheath 2 has been advanced until the self-expanding stent 34 is positioned proximate the dissection 42.

With the self-expanding stent 34 positioned at the dissection 42, the sheath 12 is withdrawn from the stent 34, so that the self-expanding stent 34 goes from being within the generally non-compliant first portion 14, to being within the compliant second portion 16, and finally out of the sheath 12. In the embodiment depicted in FIGS. 2–4, the sheath 12 is withdrawn while the stent 34 is held stationary, proximally and distally, with respect to the artery. Accordingly, as the sheath slides off of the stent 34, the stent 34 position adjacent to the dissection 42 remains generally unchanged during deployment. Alternatively, the sheath may remain stationary, so that the stent moves distally with respect to both the sheath and the site to be treated. Note that, in either case, the stent slides within the sheath relative to the sheath itself, although relative to other structures (such as the arterial dissection) the stent may in fact remain stationary while the sheath moves proximally within the artery.

As depicted in FIG. 3, as the stent 34 passes through the compliant second portion 16 and out of the sheath 12, it causes the compliant second portion 16 to flare outwardly. The second portion distal end 28 flares or "trumpets" out as compared to the second portion proximal end 26. The second portion distal end 28 achieves an enlarged diameter greater than that of the non-compliant first portion 14. Depending on the particular embodiment, the second portion distal end 28 may achieve a diameter that approaches the arterial diameter. As the stent 34 passes out of the second portion distal end 28, the stent 34 expands into contact with the arterial wall inner surface 46. The stent 34 assumes an expanded diameter 48 that holds the stent 34 in position to support and strengthen the arterial wall 44.

As depicted in FIG. 4, after the stent 34 is fully expanded and deployed in contact with the arterial inner surface 46, the sheath 12 and guidewire 45 are withdrawn from the vasculature, with the self-expanding stent 34 remaining behind in the artery 38.

All or part of the first portion 14 and/or the second portion may include materials to help assist in visualizing the stent. For example, the first portion and/or the second portion may be loaded with a radiopaque polymer for enhanced visualization under fluoroscopy.

Figure 5:
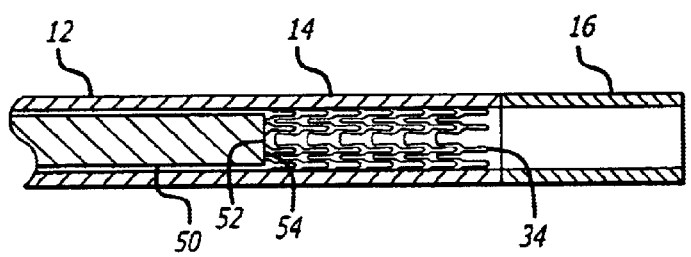
FIG. 5 is a side view, in partial cross-section, of a stent delivery system according to the present invention.

Various devices and methods can be used to move the stent 34 through the sheath 12 or, depending on the embodiment or the method or operation, to prevent the stent 34 from moving as the sheath 12 is withdrawn. For example, the stent may be pushed or pulled out of the sheath using various pushing devices and/or pulling devices. In the embodiment depicted in FIG. 5, a longitudinal rod 50 having a distal end 52 is positioned with the sheath 12 proximal of the stent 34. The rod 50 may have various configurations, including hollow or solid construction, depending on the particular application. To deploy the stent 34, the rod 50 is distally advanced within the sheath 12 until the rod distal end 52 contacts the stent proximal end 54. The rod 50 is then further distally advanced through the sheath 12, thereby pushing the stent 34 into the compliant second portion 16 and out of the sheath 12. The rod 50 may also be held in place as the sheath 12 is withdrawn, so that the rod 50 contacts the stent proximal end 54 to prevent the stent 34 from moving proximally.

Figure 6:
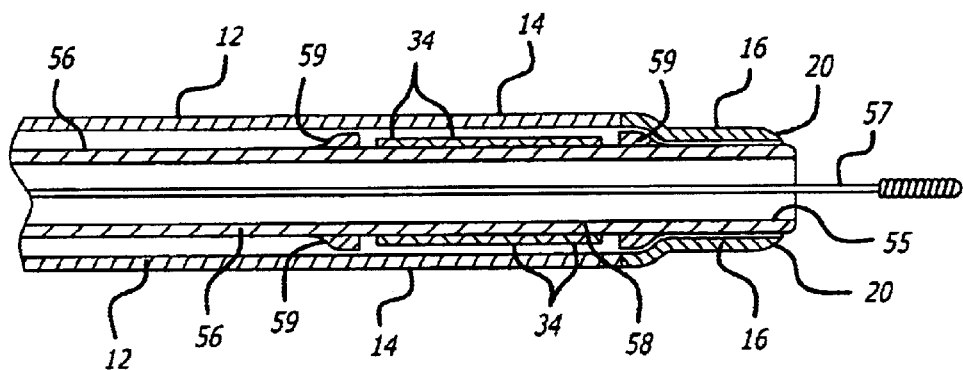
FIG. 6 is a side view, in partial cross-section, of a stent delivery system according to the present invention.

Another embodiment of the invention involves an elongated device, such as a delivery catheter, upon which the stent is mounted, with the sheath placed over the stent and elongated device and then retracted to allow the stent to expand. In the embodiment of FIG. 6, a delivery catheter 56 has a distal end portion 58 upon which the stent 34 is mounted. The delivery catheter 56 may have an inner lumen 55 in which a guidewire 57 may be positioned. The sheath 12 is placed over the stent 34 and catheter 58 so that the stent 34 is positioned within the generally non-compliant first portion 14 of the sheath 12. The distal end 20 of the sheath 12 may be tapered to form a smooth transition with the surface of the delivery catheter 56. The distal portion 16 of the sheath 12 may follow the contour of the delivery catheter 56. The delivery catheter 56 can control the longitudinal placement of the stent 34. When the sheath 12 is withdrawn from over the stent 34, as may be achieve by sliding the sheath 12 proximally along the catheter 56, the stent 34 is released and can expand.

The catheter 56 may be held securely in position as the sheath 12 is withdrawn in order to enhance the accuracy of stent placement. The delivery catheter 56 may include a restraining device to prevent the stent 34 from moving proximally and/or distally. For example, as depicted in the embodiment of FIG. 6, one or more retainer rings 59, positioned distally and/or proximally of the stent 34, help to retain the stent 34 in position. Such retainer rings 59 may be used in conjunction with, or may themselves be, marking devices formed from materials that are visible using fluoroscopy or other monitoring methods, so that a user can more easily determine the position of the delivery catheter 56 and hence of the stent 34 during deployment. Such marking devices maybe positioned on the delivery catheter, the sheath, and/or the stent itself. In another example of a stent retaining device, a delivery catheter may include a depression in which the stent is positioned to prevent longitudinal movement of the stent with respect to the delivery catheter.

In a further embodiment of the invention, the compliant second portion has varying compliance, depending on the particular area of the compliant second portion. For example, the compliance may vary along the length of the compliant second portion. One such embodiment involves a compliant second portion that is progressively more flexible from its proximal end to its distal end. The variation in compliance can be achieved using a variety of methods and techniques, including changing the materials and/or the dimensions of different portions of the compliant second portion.

Figure 7A:
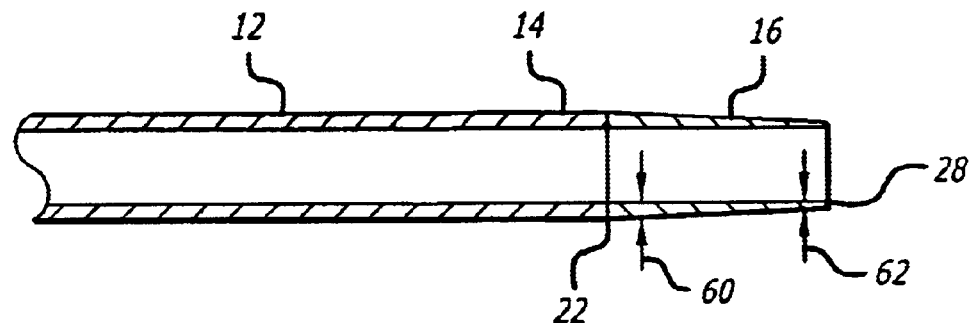
FIG. 7a is a side view, in partial cross-section, of a sheath according to the present invention.
Figure 7B:
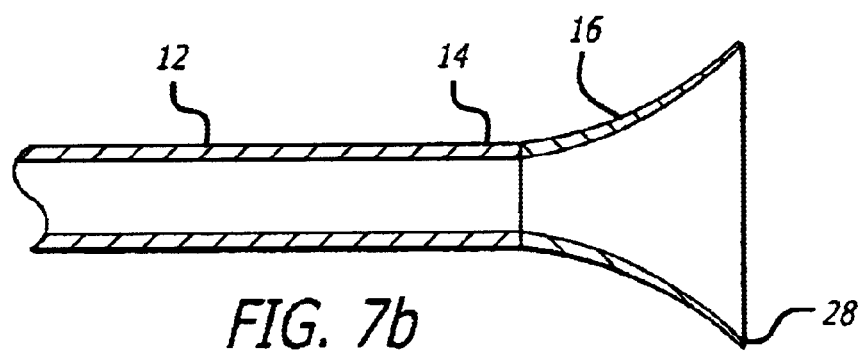

In the example depicted in FIG. 7a, the compliant second portion 16 has a proximal end 26 with a proximal thickness 60 somewhat greater than the distal thickness 62 at the distal end 28. The resulting structure has much greater compliance at the distal end 28 than at the proximal end 26. As stated, in alternative embodiments, compliance can also be altered by changing material or material properties such as orientation or crystalinity. With the increased compliance at the distal end 28, the second portion 28 can substantially flare outwardly, as depicted in FIG. 7b, when subjected to and outward expansion force such as might be created by a self-expandable stent (not shown).

Figure 8:
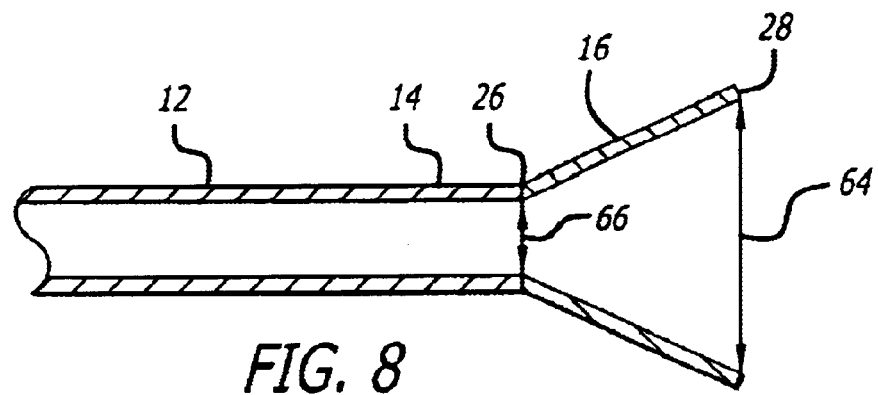
FIG. 8 is a side view, in cross-section, of a sheath according to the present invention.

FIG. 8 depicts a further embodiment of the invention, wherein the second portion 16 is preformed in a shape designed to smooth and control the expansion of a self-expanding stent. In the embodiment of FIG. 8, the second portion 16 is preformed with a generally funnel shape, so that the second portion distal end 28 has a substantially larger diameter 64 than the proximal end diameter 66. The second portion in such preformed devices may be either compliant or generally non-compliant, depending on the particular application.

The dimension and materials used to form the sheath can vary, depending on the particular application. For example, dimensions for peripheral use will vary from coronary applications, as is known in the art. The materials of construction of the sheath may be selected, for example, from those used in conventional stent delivery catheters. Polymers, including non-compliant and compliant polymers, may be used to form the sheath. The specific dimensions and materials of construction of the detachable sheath set forth herein are provided as examples, and substitutes are readily contemplated which do not depart from the invention.

The stents as described herein may be formed from any number of materials displaying shape memory characteristics, including metals, metal alloys and polymeric materials that can be constrained in a reduced delivery profile and upon release assume an enlarged deployed diameter. The stents may formed from metal alloys such as stainless steel, tantalum, or nickel-titanium (NiTi).

While the present invention has been described herein in terms of delivering an expandable stent to a desired location within a patient's blood vessel, the delivery system can be employed to deliver stents to locations within other body lumens such as urethra or Fallopian tubes so that the stents can be expanded to maintain the patency of these body lumens. It will therefore be apparent from the foregoing that while particular forms of the invention have been illustrated and described, various modifications can be without departing from the spirit and scope of the invention. Accordingly, it is not intended that the invention be limited, except as by the appended claims.

What is claimed:

1. A stent delivery assembly, comprising:
   a tubular sheath having a longitudinal axis, said tubular sheath having a first portion with a first compliance and a second portion with a second compliance, wherein the second compliance is greater than the first compliance, and wherein the second portion includes a terminal end that is tubular and that is continuous about its circumference; and
   a self-expanding stent disposed within the first portion of the generally tubular sheath.

2. The assembly of claim 1, wherein:
   the first compliance is sufficiently low to prevent the self-expanding stent from expanding while the self-expanding stent is positioned within the first portion.

3. The assembly of claim 2, wherein:
   the first compliance is essentially zero.

4. The assembly of claim 1, wherein:
   the first portion of the generally tubular sheath has a proximal end and a distal end, the second portion of the tubular sheath is adjacent to the distal end of the first portion, and the stent is positioned in the first portion adjacent to the distal end of the first portion.

5. The assembly of claim 4, wherein:
   the self-expanding stent is slidably positioned within the first portion, and the generally tubular sheath is configured to permit the self-expanding stent to be slid from the first portion to the second portion.

6. The assembly of claim 5, wherein:
   the generally tubular member is configured to permit the self-expanding stent to be slid through the second portion and out of the generally tubular member.

\* \* \* \* \*